US009370605B2

(12) United States Patent
Zhang et al.

(10) Patent No.: US 9,370,605 B2
(45) Date of Patent: Jun. 21, 2016

(54) COBALT CHROME COATED TITANIUM IMPLANT

(71) Applicant: Howmedica Osteonics Corp., Mahwah, NJ (US)

(72) Inventors: Zongtao Zhang, Riverdale, NJ (US); Keenan Michael Hanson, Tuxedo, NY (US); Thomas Francis McCarthy, Neshanic Station, NJ (US); Daniel E. Lawrynowicz, Monroe, NY (US); Aiguo Wang, Wayne, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 517 days.

(21) Appl. No.: 13/783,894

(22) Filed: Mar. 4, 2013

(65) Prior Publication Data
US 2014/0249642 A1    Sep. 4, 2014

(51) Int. Cl.
*A61L 27/30* (2006.01)
*A61F 2/34* (2006.01)
*A61L 27/06* (2006.01)
*A61F 2/30* (2006.01)
*A61F 2/32* (2006.01)
*C23C 14/16* (2006.01)

(52) U.S. Cl.
CPC .......... *A61L 27/306* (2013.01); *A61F 2/30767* (2013.01); *A61F 2/32* (2013.01); *A61L 27/06* (2013.01); *C23C 14/16* (2013.01); *A61F 2002/3098* (2013.01); *A61F 2002/30934* (2013.01); *A61F 2002/3208* (2013.01); *A61F 2310/00023* (2013.01); *A61F 2310/00413* (2013.01); *A61L 2420/02* (2013.01); *A61L 2420/08* (2013.01); *A61L 2430/02* (2013.01)

(58) Field of Classification Search
CPC ................... C23C 14/165; A61F 2002/3098; A61F 2310/4013; A61L 27/045; A61L 27/28
USPC ........................................ 427/2.24, 2.26, 2.27
See application file for complete search history.

(56) References Cited

U.S. PATENT DOCUMENTS

| 4,145,764 A * | 3/1979 | Suzuki et al. ................ 623/23.6 |
| 4,798,610 A | 1/1989 | Averill et al. |
| 4,798,765 A | 1/1989 | Ishizaka et al. |

(Continued)

OTHER PUBLICATIONS

Patel et al. Cobalt-based orthopaedic alloys: Relationship between forming route, microstructure and tribological performance. Materials Science and Engineering C32 (2012) pp. 1222-1229.*
Brunette et al., Titanium in Medicine, Material Science, Surface Science, Springer, 10.2 Physical Vapor Deposition, pp. 282-341, 2001.

(Continued)

*Primary Examiner* — Cachet Sellman
(74) *Attorney, Agent, or Firm* — Lerner, David, Littenberg, Krumholz & Mentlik, LLP

(57) ABSTRACT

A method for coating an orthopedic implant made of a titanium or titanium alloy substrate with a cobalt-chrome molybdenum alloy uses multi-arc physical vapor deposition (MA-PVD). The substrate has a first bearing surface coated with a coating made of the deposited cobalt-chromium molybdenum alloy. The bearing surface slidably receives a second bearing surface of the prosthetic joint component. The MA-PVD cobalt-chromium molybdenum alloy coating forming the first bearing surface is made up of hexagonal close packed (HCP) grains having a columnar structure with a length of about 1 µm and a width of about 0.1 µm with the length of each HCP grains being oriented generally perpendicular to the titanium substrate bearing surface.

12 Claims, 8 Drawing Sheets

(56) References Cited

U.S. PATENT DOCUMENTS

| | | | |
|---|---|---|---|
| 4,814,239 | A | 3/1989 | Inoue et al. |
| 5,077,140 | A | 12/1991 | Luthra et al. |
| 5,098,540 | A | 3/1992 | McKee |
| 5,323,954 | A | 6/1994 | Shetty et al. |
| 5,441,537 | A * | 8/1995 | Kenna ............... 419/2 |
| 5,861,042 | A | 1/1999 | Buechel et al. |
| 5,955,151 | A | 9/1999 | Hajmrle et al. |
| 6,261,322 | B1 | 7/2001 | Despres, III et al. |
| 6,827,742 | B2 | 12/2004 | Hayes, Jr. et al. |
| 7,455,694 | B2 | 11/2008 | Epaules et al. |
| 7,458,991 | B2 | 12/2008 | Wang et al. |
| 7,513,912 | B2 | 4/2009 | Hayes, Jr. et al. |
| 7,520,902 | B2 | 4/2009 | Deloge et al. |
| 7,833,276 | B2 | 11/2010 | Auxepaules et al. |
| 7,850,738 | B2 | 12/2010 | Hayes, Jr. et al. |
| 2002/0052659 | A1 | 5/2002 | Hayes et al. |
| 2007/0191962 | A1 | 8/2007 | Jones et al. |
| 2009/0012624 | A1 | 1/2009 | Overholser et al. |
| 2010/0291401 | A1 * | 11/2010 | Medina et al. ............... 428/593 |
| 2011/0066253 | A1 | 3/2011 | Langhorn et al. |
| 2012/0209398 | A1 | 8/2012 | Richardson et al. |

OTHER PUBLICATIONS

Extended European Search Report for Application No. 14157132.3 dated Jun. 26, 2014.
Arcam EBM System, ASTM F75 CoCr Alloy, undated.
Badita, Proceesings of International Conference on Innovations, MECAHITECH' 11, vol. 3, pp. 234-239, 2011.
Capitanu et al., SERBIATRIB '11, 12th International Conference on Tribology, Kragujevac Serbia, pp. 267-273, May 11-13, 2011.
Chiesa et al., J Bone Joint Surgery Br, vol. 90B, No. Supp 160, 2008, 2 pages.
Deloro Stellite, Stellite 6 Alloy, 2008.
Galetz et al., J Biomed Mater Res, Part B, Appl Biomater 93B, pp. 244-251, 2010.
Garcia et al., Metallurgical and Materials Trasnactions A, vol. 30A, pp. 1999-1177, May 1999.
Gonzales-Mora et al., J Biomedical Science and Engineering, 4, pp. 651-656, 2011.
Hendry et al., J Biomed Mater Res, 58, pp. 156-166, 2001.
Krishna et al., Scient Direct, Acta Biomaterialia 4, pp. 697-706, 2008.
Lee et al., Wear, 267, pp. 1915-1921, 2009.

\* cited by examiner

PVD CoCr COATING CHEMICAL COMPOSITION

| ELEMENT | COMPOSITION (WEIGHT %, AVERAGE) | | | | |
|---|---|---|---|---|---|
| SAMPLE | CoCrMo | TARGET | PVD COATING | ASTM 1537 REQUIREMENT | |
| METHOD | CHEM | EDS | EDS | MIN | MAX |
| CHROMIUM | 27.8 | 27.7 | 27.9 | 26 | 30 |
| MOLYBDENUM | 5.5 | 5.5 | 5.4 | 5 | 7 |
| MANGANESE | 0.7 | 0.7 | 0.8 | 0 | 1 |
| IRON | 0.4 | 0.6 | 0.1 | 0.00 | 0.75 |
| NICKEL | 0.5 | 0.9 | 0.5 | - | 1.0 |

FIG. 1

IMAGE QUALITY (IQ) MAP OF THE ELECTRON BACKSCATTER DIFFRACTION PATTERNS COLLECTED AT EACH PIXEL FOR PVD CoCrMo COATING TOP VIEW (LEFT) AND CROSS-SECTION VIEW (RIGHT). COLUMNAR GRAINS ARE ABOUT 1 μm LONG AND 0.1 μm WIDE, PERPENTICULAR TO SUBSTRATE.

SEM OF FRACTURED PVD COATING SHOWS
COLUMN GRAINS PERPENTICULAR TO SUBSTRATE.

VICKERS HARDNESS DISTRIBUTION AT VARIOUS LOADS

TENSILE BOND STRENGTH OF PVD CoCr ON CP-Ti vs SOAKING TIME IN 40°C.
ALL ARE ADHESIVE FAILURE INSIDE PEEK FILM, NOT AT CoCr/Ti INTERFACE.
NO CORROSION OCCURS.

COBALT CHROME COATED TITANIUM IMPLANT

BACKGROUND OF THE INVENTION

This invention relates to a bearing surface for an orthopedic implant which is made of a Cobalt Chrome molybdenum alloy coating deposited on a titanium (Ti) substrate.

In the 1960's to the 1990's, smaller head size metal-on-UHMWPE bearings (22-28 mm) were widely used in orthopedic industry based on Dr. John Chanley's low wear and low friction concepts, but the small size bearing had a high dislocation rate. Between 2000-2010, larger size metal-on-metal bearing (32-44 mm) were used. These significantly decreased the dislocation rate. In recent years, Stryker Corp. introduced dual mobility or bi-polar acetabular cup systems, which combined all benefits of both small bearings' low friction and large bearings' low dislocation rate.

It is desirable to make a new dual mobility cup that has the combined functional features of the current dual mobility acetabular cups, especially having a 3D titanium foam structure for bone ingrowth, while the bearing surface maintains the use of CoCr as a wear resistant surface. Dual mobility acetabular cups are shown in U.S. Pat. Nos. 7,455,694 and 7,833,276.

One solution is using an existing Titanium shell with a thin film Cobalt chromium molybdenum coating (CoCr). These materials have been approved by FDA in biocompatibility. The Titanium shell can be easily machined into any geometry. Physical vapor deposition (PVD) is an approved technology used in the orthopedic area.

In the past CoCr coating have been made on CoCr substrates for orthopedic bearing applications. These coatings had Co, 28% Cr and 6% Mo composition (ASTM F1537, F75) and were made by magnetron sputtering PVD (MS-PVD).

R. Chiesa, C. Piconi, L. Chiusoli, and L. Vandini in "Surface Treatment For Wear Minimization In A New Design Of Total Knee Replacement", J. Bone Joint Surg Br 2008 Vol. 90-B No. suppl 160 reported magnetron sputtering physical vapor deposition CoCr on cast CoCr knee surface and conducted knee wear simulator test. The purpose of this study was using CoCr coating to minimize the defects of cast CoCr bearing surface, only abstract was published.

Liliana Badita et al., Lucian Capitano, Liliana Laura Badita, Dumitru Catalin Bursuc, "Damage Of The Co—Cr—Mo Femoral Head Of A Total Hip Prosthesis And Its Influence On The Wear Mechanism," 12th International Conference on Tribology, Kragujevac, Serbia, 11-13 May 2011, p. 267-273, Victor A. Gonzalez-Mora, Michael Hoffmann, Rien Stroosnijder, F. Javier Gil, "The Role Of Hardness And Roughness On The Wear Of Different CoCrMo Counterfaces On UHMWPE For Artificial Joints," J. Biomed Sci. and Eng., 2011, 4, 651-656, all reported clinical retrieval studies of MS-PVD CoCr coating on CoCr femoral heads against UHMWPE. They found that after testing the CoCr coating had scratching, cracking, peeling and having tribocorrosion. Also the CoCr coated heads had different hardnesses on the CoCr surface in different locations, ranging from lowest 51.2 HRC (about 528 Vickers) in one location to the highest 61.8 HRC (about 720 Vicker) in another. Spherity inspection showed the coated head had an ovoid shape. Post revision inspection indicated that some area of CoCr coating was completely destroyed.

Victor A. Gonzalez-Mora et al., Liliana Laura Badita, Tribologgical Characterization Of Materials used For Femoral Heads Of Hip Prostheses" proceeding of international conference on innovation recent trends and challenges in mechanics, mechanical engineering and new high-tech products development, MECAHIGHTECH'11, vol. 3, 2011 did a pin-on-Disc wear study of UHMWPE-on-MS-PVD CoCr coated rough CoCr coupons. They did not indicate what kind of PVD method was used for CoCr coating, but reported the coating hardness 884±28 Vickers and surface roughness 100 nm. The wear test was conducted using the pin-on-disc method at 1 Mc at a contact stress 3.54 Mpa in Bovine serum water solution. The CoCr coating did not spall at end of test, but MS-PVD CoCr coating showed highest wear rate of UHMWPE, as compared to mass finished cast CoCr and wrought CoCr. The author attributed high wear rate of UHMWPE to the CoCr coating delamination during the wear testing. The delaminated CoCr particles contributed to third body wear. However, the CoCr coating appeared to be either not polished, or poorly polished, Ra=0.1 micron (100 nm) according to atomic force microscopy. This surface roughness doubled the surface roughness of mass finished CoCr 50 nm, therefore the wear rate conclusions were not comparable. All the above studies were preliminary without detailed manufacturing and test details.

Overall, the MS-PVD CoCr coatings performed worse than conventional bulk CoCr as bearing surfaces. One factor may be attributed to the MS-PVD process itself, which is more suitable for flat surfaces such as magnetic recording discs but not for spherical surfaces. Another factor is the low bond strength of the coating to the substrate. MS-PVD process has very low deposition rate. Also, CoCr coating on CoCr substrate does not introduce any new function to the device. It makes no sense from a commercial point of view.

"Bimetal orthopedic devices," are known which were composed of bimetal structure of CoCr and Ti structure, Daniel E. E. Hayes, Jr., Alfred S. Depress, III, "Bimetal Tibial Components Construct For Knee Joint Prosthesis," Hayes Medical, Inc., U.S. Pat. No. 7,513,912, Alfred S. Despress, Eugene J. Elwod, Robert R. Aharonov, Peter Ehlers, Knut Andersen, "Implant With Composite Coating," Hayes Medical Inc., U.S. Pat. No. 6,261,322, Daniel E. E. Hayes, Jr., Alfred S. Depress, III, "Bimetal Acetabular Component Construct For Hip Joint Prostheses," Hayes Medical Inc., U.S. Pat. No. 6,827,742, H. Ravindranath Shetty, Jack E. Parr, "Method Of Bonding Titanium To A CoCr Based Alloy Substrate In An Orthopedic Implant Device," U.S. Pat. No. 5,323,954, Daniel E. E. Hayes, Jr., Alfred S. Depress, III, "Bimetal Acetabular Component Construct For Hip Joint Prostheses, Hayes Medical Inc., U.S. Pat. No. 7,850,738. In these publications the main orthopedic device structure was CoCr, which provided both structural and wear resistance against UMPWPE, while a Ti coating was used for better bone ingrowth. The multi-arc PVD method was used to make a Ti coating not a CoCr coating for wear resistance.

Coating Ti on CoCr substrate has been used in the orthopedic industry for decades. However, there are shortcoming such as the stress-shielding of the stiff CoCr construct, the drop in fatigue strength as well as the high weight of the total device, D. M. Brunette, P. Tengvall, M. Textor, P. Thmsen, "Titanium In Medicine," Spinger Verlag Birlin Heidelberg, pages 283-341, 703-777 (2001).

Another coating used in the past is perpendicular magnetic recording CoCr film, which was invented in the 1980's made by MS-PVD, Kazuo Inoue, Noboru Watanabe, Kazuo Kimura, Eiichiro Imaoka Sagamihara, "Perpendicular Magnetic Recording Medium," U.S. Pat. No. 4,798,765. The purpose of the technology was to make a columnar structured CoCr thin film (about 0.5 μm) that had grains orientation perpendicular to the magnetic disc surface. This was done so that the film had a maximum recording density and high coercive force in the vertical direction, while the film maintained lowest magnetic remains in the parallel direction. This coating composition is about 84% cobalt and 16% chrome. Because implants are submerged in highly corrosive body fluid at 37° C., this magnetic recording CoCr film is not suitable for orthopedic implant applications.

Yet another coating was CoCr films on titanium for oxidation resistance of a titanium alloy. This use is for high temperature turbine applications, Douglas W. Mckee, "Method For Depositing Chromium Coating For Titanium Oxidation Protection," U.S. Pat. No. 5,098,540, Krshan, L. Luthra, Douglas W. Mckee, "Coating Systems For Titanium Oxidation Protection," U.S. Pat. No. 5,077,140, Karel Hajmrle, Anthony P. Chilkowich, "Low Friction Cobalt Based Coatings For Titanium Alloys," U.S. Pat. No. 5,955,151. The composition of the coating is Cr, CoCrAl, CoNiCr, CoCrAlY-BN. The coating methods are MS-PVD, thermal spray. All these coating compositions are not appropriate for implant applications.

Still another coating is called "thick CoCr coating on titanium alloy by thermal spray." This technology was described in Stellite® 21 CoCr alloy product brochure (http://www.stellite.co.uk/portals/o/stellite%206%20Final.pdf), but never put into practical use, Frederick F. Buechel, Michael J. Pappas, "Prosthesis With Biologically Inert Wear Resistant Surface," U.S. Pat. No. 5,861,042 in orthopedic industry. These thermal sprayed coatings obviously had low hardness (470-522 VHN 300 g) and bond strength about 9000-11000 psi (62-76 Mpa). This coating is also unsuitable for use as an orthopedic bearing surface because it has 10 times corrosion rate of as-forged CoCr (ASTM) 1537) according to tests performed by the inventors.

A sixth category of coating is thin ceramic coatings on Ti substrate for orthopedic bearing applications, D. M. Brunette, P. Tengvall, M. Textor, P. Thmsen, "Titanium In Medicine," Springer Verlag Birlin Heidelberg, pages 283-341, 703-777 (2001), Jason B. Langhorn, Ronald Overholser, Bryan Smith, "Ceramic Coated Orthopedic Implant And Method Of Making Such Implants," US 2011/0066253. The most popular coating was TiN. The only use is for CrN/ZrN thin film coating on CoCr substrates (http://www.aesculapimplantsystems.com/assets/base/doc/DOC832-ASKneeBrochure.pdf). This mentions that the TiN coated Ti6A14V substrate improved abrasion resistance, but was seen to delaminate after around 600,000 cycles in orthopedic articulating surface. All the ceramic coatings were brittle when on a soft titanium substrate, which caused fatigue failure. On the other hand, if using CoCr alloy substrate, the stiff substrate supports thin ceramic coating well, i.e., low Young's modulus ratio of coating to substrate. This could be the reason why thin ceramic coatings have been commercialized on CoCr substrates.

Another prior art coating is using the CoCr alloy itself. Hexagonal close-packed (HCP) phase is harder than face center cubic (fcc) phase. HCP phase is preferred as a bearing surface to increase scratch resistance, but it is hard to form. The hardness of material is linearly increased with the percentage of HCP phase. The maximum hardness (45 HRC) can be obtained when the HCP phase is close to 95% produced by a long annealing time at high temperature, such as 800° C. for 10 hours (A. De J. Saldivar, et al., "Formation of hcp martensite during the isothermal again of an fcc Co-27 Cr-5Mo-005C orthopedic implant alloy," Metallurgical and Materials Transaction A, Vol. 30A, 1177-1184 (1999). However, for normal casting, wrought, or forging operation, the majority CoCr stays as the fcc phase with only a minor HCP phase.

Up to now, no commercial orthopedic device has a coating with a percentage of HCP CoCr phase on bearing surface.

It has been unexpectedly found that a CoCr thin film can be produced on a titanium shell for an acetabular cup using multi-arc physical vapor deposition (MA-PVD). The major advantages of MA-PVD are its high deposition efficiency and ability to be used on all geometries, especially for concave acetabular cups.

BRIEF SUMMARY OF THE INVENTION

It was found that the CoCr coating produced by the method of the present invention as a bearing surface on titanium was dense with small percentage isolated pores (>99% relative density). It has the same chemical composition and corrosion resistance as forged ASTM F1537 CoCr alloys. Using an advanced electron back scattered diffraction (EBSD) analytical tool, it was discovered that the coating had unique characteristics of 0.1-1 μm gain size, primary hexagonal close packed (HCP) phase, and vertical grain orientation in the HCP direction, which is different from convention forged CoCr having 5-50 μm grain size, majority face centered cubic (FCC) phase, and random grain orientation. The special grain structure resulted in 814±64 Vickers hardness at 25 g load. This is significantly higher than 470±14 Vickers of F1537 CoCr forged cup at the same load.

Because of the high hardness, the CoCr coating was scratched less depth (6.5 μm) than forged CoCr (9.3 μm) under a clinically relevant 30 N load using a diamond stylus. This means that the CoCr coating of the present invention is more wear resistant than a standard bulk CoCr bearing surface against a third body. In addition, with a coating thickness of 13 μm, the scratch only penetrated half of the coating thickness, and thus the CoCr coating of the present invention has better third body wear resistance than predicted for a CoCr forged cup.

The advantage of the multi-arc PVD process is a high deposition efficiency and suitability for coating concave cup inner sphere geometries, as compared to other PVD processes. The coating process mapping has demonstrated the coating uniformity in the different locations in a production equipment chamber. The coating thickness of 16-19 μm in the inner sphere of a forced CoCr cup was achieved. The coating was able to be polished to 13 μm with a mirror finish (Ra<20 nm).

The PVD CoCr coating of the present invention has a strong interface bonding. The adhesive tensile bond strength was over 110 Mpa on blasted surfaces. The bond strength did not change in simulated body fluid at 22 weeks soaking. A Mercedes test indicated the highest grade interface bonding (F1). A bending crack test further demonstrated that the CoCr coating of the present invention did not crack until the Ti6A14V substrate cracked. A diamond scratch test did not show CoCr coating cracking and debonding at the interface after diamond stylus scratch through the 9 μm CoCr coating under 55N critical loads. Only plastic deformation was observed of the CoCr coating in SEM. As a comparison, an oxidized Zirconium coating was cracked at 30 N critical load. Note that the Zirconium oxide coating has a total 9 μm hard coatings, a 4.0 μm Zirconium oxide layer and a 5.0 μm diffusion layer. The PVD CoCr coating of the present invention was strongly bonded to titanium substrate. It is believed that low residual stress (47 ski tensile) and possible atomic diffusion at interface contributed to the high bond strength. In turn, the high bond strength makes the coating process benign and allows a broad band of coating thickness. The coating did not show any sign of spalling at micrometer thickness. As a comparison, there has been reported CoCrMo coating delimination on CoCrMo femoral heads in vivo with a coating deposited by magnetron sputtering physical vapor deposition.

An important concern for any coating technology is the interfacial fatigue failure. A PVD CoCr coated PSF Tritanium ADM cup with 4.0 total wall thicknesses was tested under sphere contact fatigue using a dual mobility cup with a 28 mm CoCr head and 56 mm×3 linear by Jim Model. It passed 10 Mc without damage. Neither cracking nor coating spalling occurred in one body weight condition. Impingement between a Ti6A14V stem and a PVD CoCr coated Stryker Corp. PSF Tritanium ADM cup were tested at a contact stress level higher than yield strength of Ti6A14V substrate. Again, no coating spalling was found.

Polishing the thin PVD CoCr film coatings media polishing process, sequential grade SiC wheel grinding and followed by $Al_2O_3$ slurry polishing processing have been utilized as one of the possible processes. A one-step soft wheel polishing process can polish the CoCr coating to the same surface roughness to the forged CoCr. The inner diameter CoCr coating of Titanium acetabular cup was polished to 13 μm thickness with coating thickness removal of 3-5 μm. The soft wheel polish and media finish make thin coating polishing feasible and prevents polishing through the coating. They also reduce costs as compared to two-step process of conventional grinding and polishing.

Various aspects of the invention are accomplished by a method for manufacturing a prosthetic implant including providing a substrate made of titanium. A surface of the substrate is coated with a cobalt chromium molybdenum alloy by multi-arc physical vapor deposition to produce a majority of grains having a hexagonal close pack (HCP) phase. The cobalt chromium molybdenum HCP coating was polished. The grain sizes are between 0.1 and 1.0 μm wherein the substrate is made from commercially pure titanium or a titanium alloy wherein the HCP grains have a columnar grain structure wherein the grains have a length which is perpendicular to the substrate surface. The columnar grains are about 1 μm long and 0.1 μm wide. The polishing is performed by a polishing process selected from the group consisting of a media polishing process, a sequential grade SiC wheel grinding followed by an $Al_2O_3$ slump polishing process or a soft wheel polishing process. The polished cobalt chrome HCP coating has a hardness greater than 500Vickers Diamond Pyramid Hardness (DPH) at a 25 g load. The surface roughness is Ra<50 nm after polishing preferably having a surface roughness Ra<25 nm wherein the coating is greater than 30% chromium plus molybdenum.

Other aspects of the invention are achieved by an orthopedic implant in the form of a prosthetic joint component with a titanium or titanium alloy substrate. The substrate has a first bearing surface coated with a cobalt-chromium molybdenum alloy coating. The bearing surface slidably receives a second bearing surface of the prosthetic joint component. The cobalt-chromium molybdenum alloy first bearing surface is made of hexagonal close packed (HCP) grains having a columnar structure with a length of about 1 μm and a width of about 0.1 nm with the length of each HCP grains is oriented generally perpendicular to the substrate bearing surface. The cobalt-chromium molybdenum alloy bearing surface has a surface roughness (Ra) less than 50 nm. The cobalt chrome bearing surface has a thickness greater than 5 μm and a surface hardness greater than 500Vickers Diamond Pyramid Hardness (DPH) at 25 g load. The cobalt-chrome alloy comprises at least 90% cobalt-chrome. The prosthetic joint also includes a component selected from the group consisting of ultrahigh molecular weight polyethylene, poly ether ether ketone, or a cobalt-chrome molybdenum alloy. The cobalt chrome molybdenum alloy coating is between 6 and 100 μm thick before polishing. The cobalt chrome molybdenum alloy coating is between 5 and 95 μm thick after polishing.

Other aspects of the invention are provided by an orthopedic implant having an acetabular cup shell having a first part-spherical bearing surface and a bone contacting surface. The bearing surface coated with a coating comprising a cobalt-chromium molybdenum alloy. The bearing surface slidably receives a second part-spherical bearing surface of a prosthetic joint component. The cobalt-chromium molybdenum alloy first part-spherical bearing surface comprising hexagonal close packed (HCP) grains having a columnar structure with a length of about 1 μm and a width of about 0.1 μm with the length of each HCP grains is oriented generally perpendicular to the substrate bearing surface. The shell bone contacting surface may have a tissue-ingrowth surface formed thereon by any known process.

BRIEF DESCRIPTION OF THE DRAWINGS

FIG. 1 is a table showing the chemical compositions of a standard cobalt-chrome molybdenum alloy used in orthopedic implants, the PVD coating of the present invention and the ASTM 1537 cobalt-chrome molybdenum for orthopedic implant specification requirements;

DETAILED DESCRIPTION

Referring to FIG. 1, there is shown the chemical composition of the PVD cobalt-chrome molybdenum coating of the present invention compared to a forged cobalt-chrome molybdenum implant material meeting the requirements of ASTM 1537. It can be seen that in all of the top five components of the alloy the coating of the present invention is within the ASTM specification requirements. The analysis of the CoCrMo coating was performed both chemically and by energy-dispersive x-ray spectroscopy.

Figure 2:
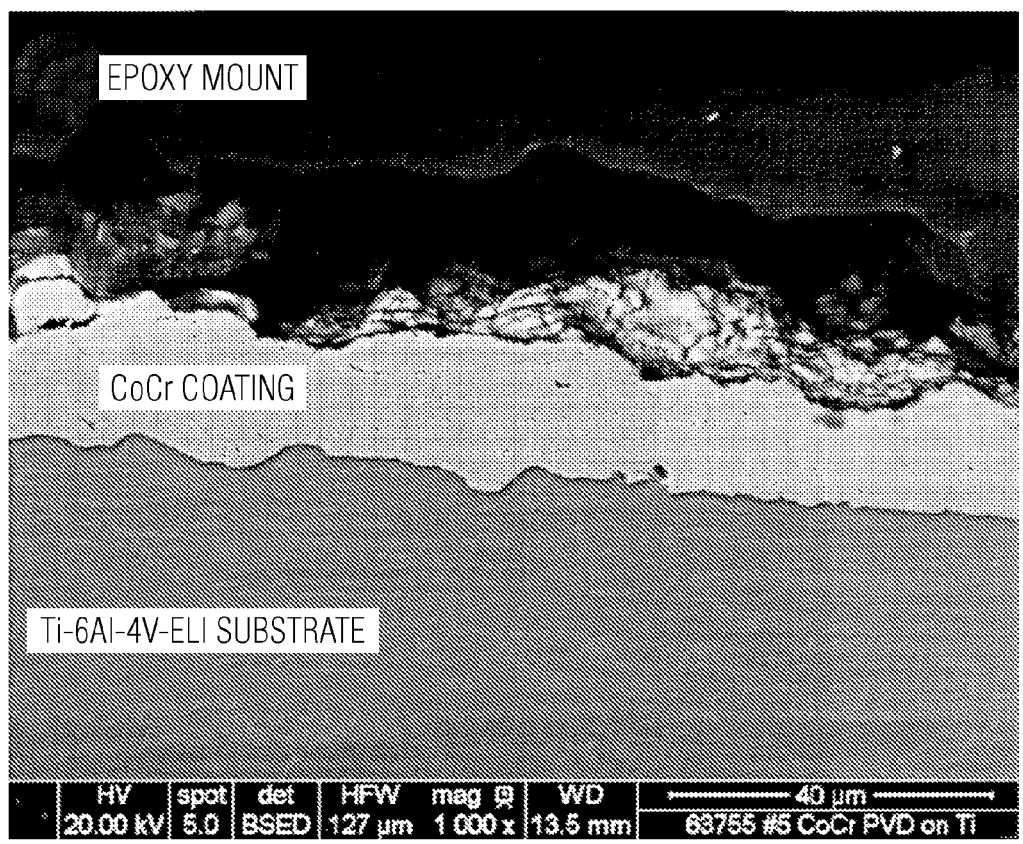
FIG. 2 is a scanning electron microscope picture of a cross-section of the PVD coating of the present invention.

Referring to FIG. 2 there is a scanning electron microscope photograph of a cross-section of the coating which was approximately 23.5 microns thick. The substrate was commercially available titanium alloy Ti6Al4VELI.

Figure 3:
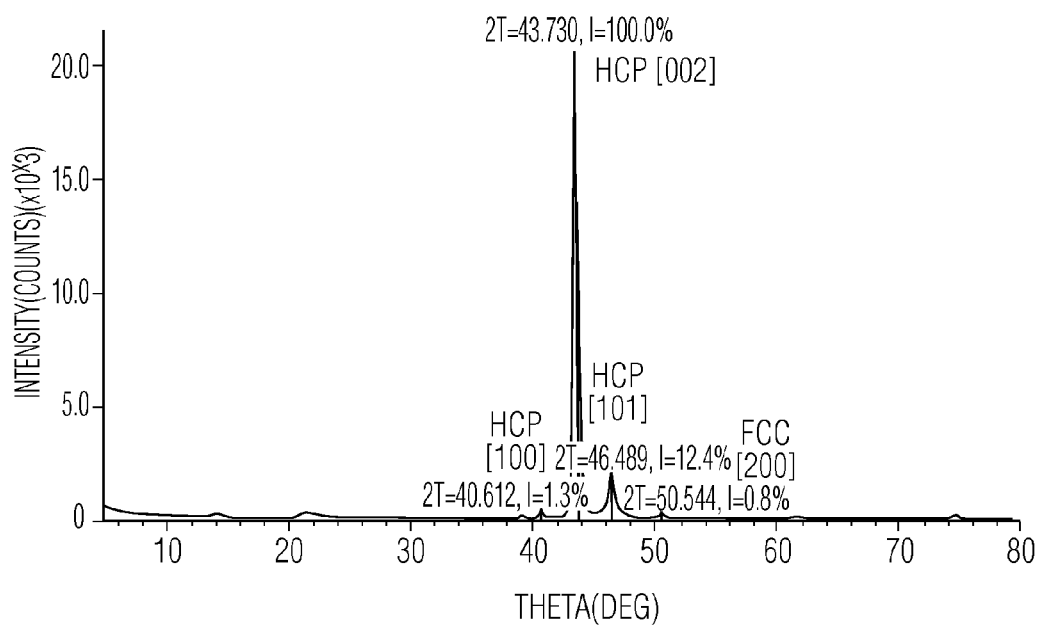
FIG. 3 shows an x-ray defraction pattern of the PVD coating of the present invention dominated by the hexagonal close packed (HCP) phase.

Referring to FIG. 3 there is an x-ray defraction pattern showing that the PVD coating of the present invention has a very high percentage of hexagonally-close-packed phase. This is exactly the opposite of standard forged cobalt-chrome molybdenum implant alloys which have a face centered cubic (FCC) phase.

Figure 4:
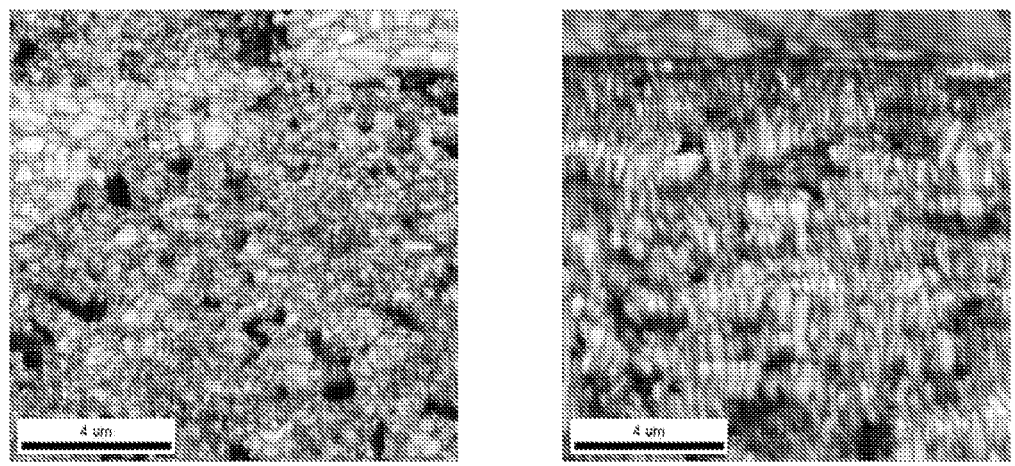
FIG. 4 shows two electron backscatter diffraction patterns for the PVD coating of the present invention with a top view to the left and a cross-sectional view to the right as well as a fracture cross-section SEM (Scanning Electron Microscope) picture with grain orientation at HCP [002] to the bottom.
Figure 4A:
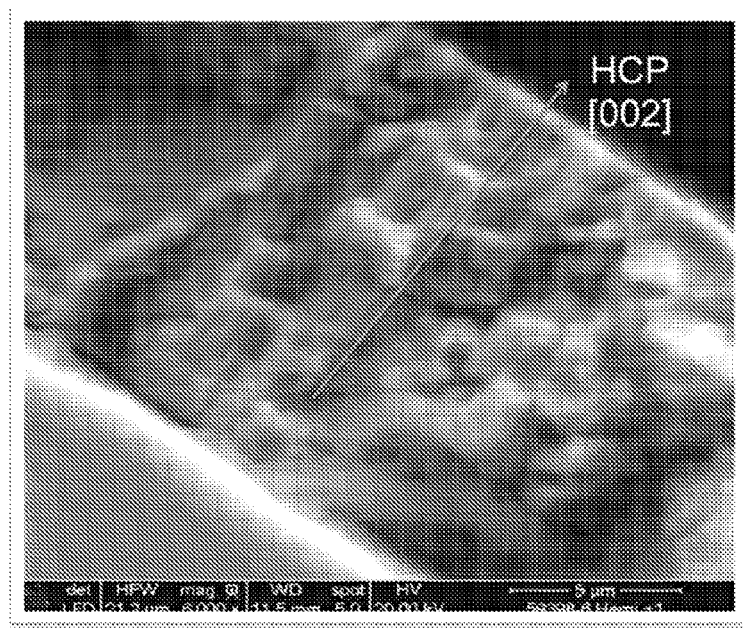
FIG. 4A is a SEM of a fractured PVD coating showing column grains perpendicular to the substitute.

Referring to FIG. 4, there is shown the electron backscatter defraction patterns for the coating of the present invention which, as shown in the cross-sectional view to the right includes columnar grains about 1 μm long and 0.1 μm wide with the columns extending perpendicular to the substrate. Fractured PVD CoCr coating also shows the column structure. It is believed the columnar structure provides, when polished, a more scratch resistant surface.

Figure 5:
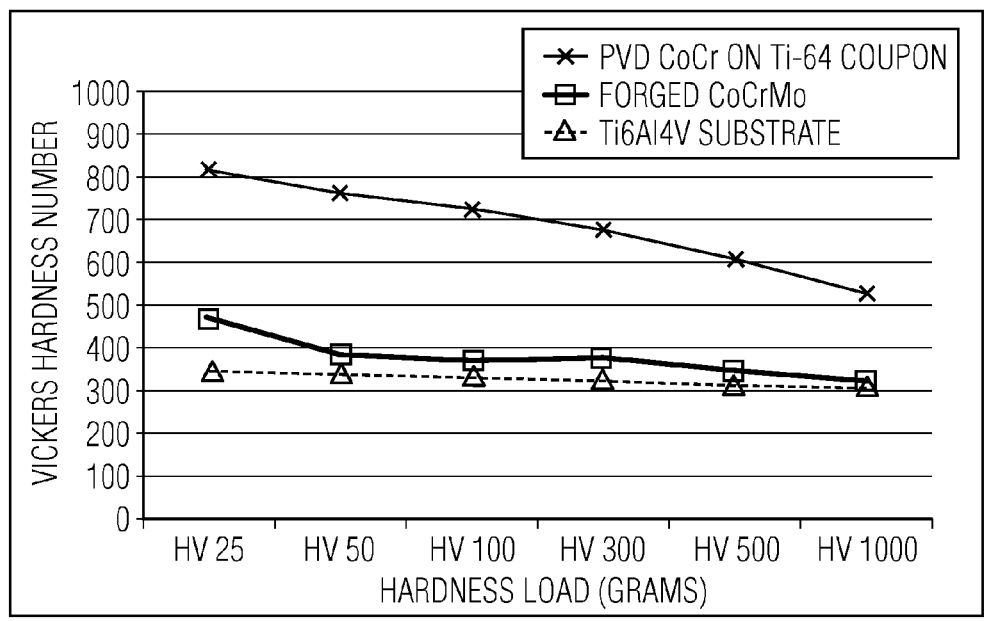
FIG. 5 shows the Vickers hardness distribution at various loads for the PVD coating of the present invention on a TI-64 coupon, a forged cobalt-chrome molybdenum implant alloy and a titanium substrate.

Referring to FIG. 5, there is shown a Vickers hardness distribution at various loads. The PVD cobalt-chrome molybdenum coating of the present invention is on a titanium alloy coupon and is compared with a forged cobalt-chrome molybdenum implant material and shows that the coating of the present invention has a superior hardness under all loads when compared to the forged cobalt-chrome molybdenum alloy and with the titanium 6AL4V substrate.

Figure 6:
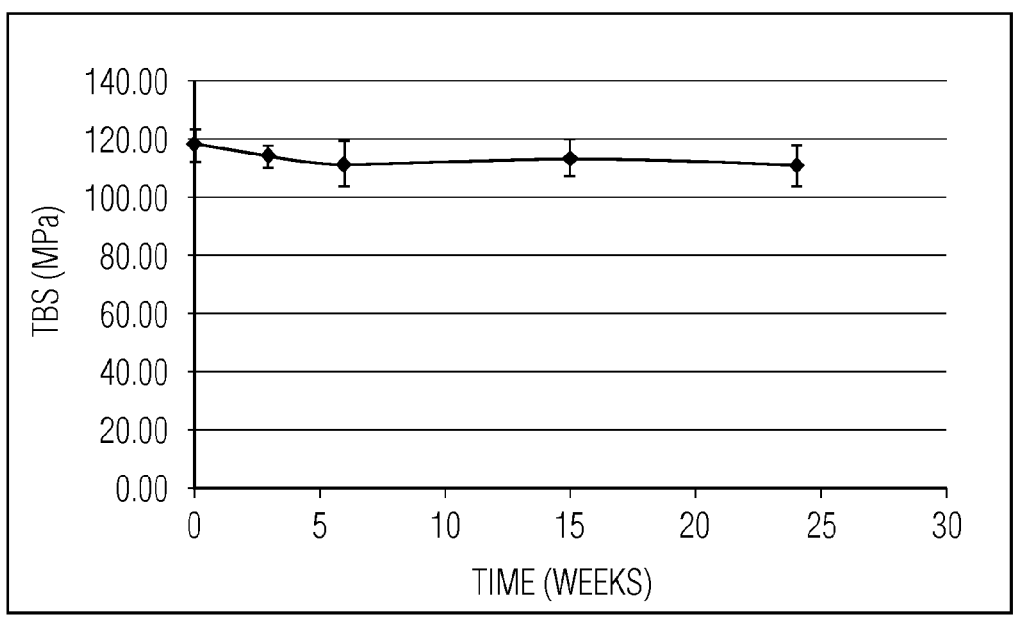
FIG. 6 shows the tensile bond strength of the PVD coating of the present invention on commercially pure titanium versus soaking time at 40° C. in simulated body fluid.
Figure 7:
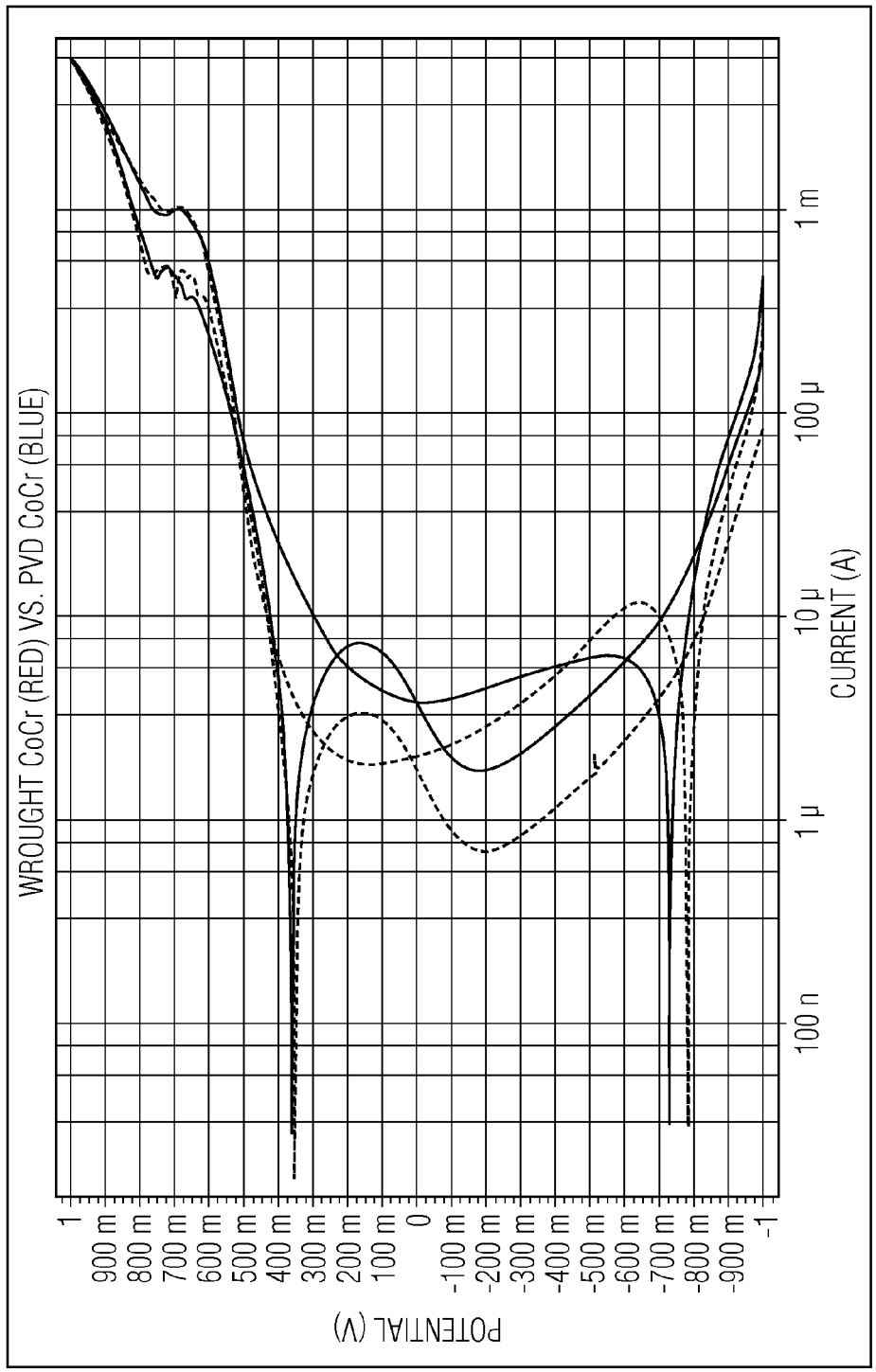
FIG. 7 shows polarization tests of PVD CoCr coating as compared to wrought CoCr (ASTM1537).
Figure 8:
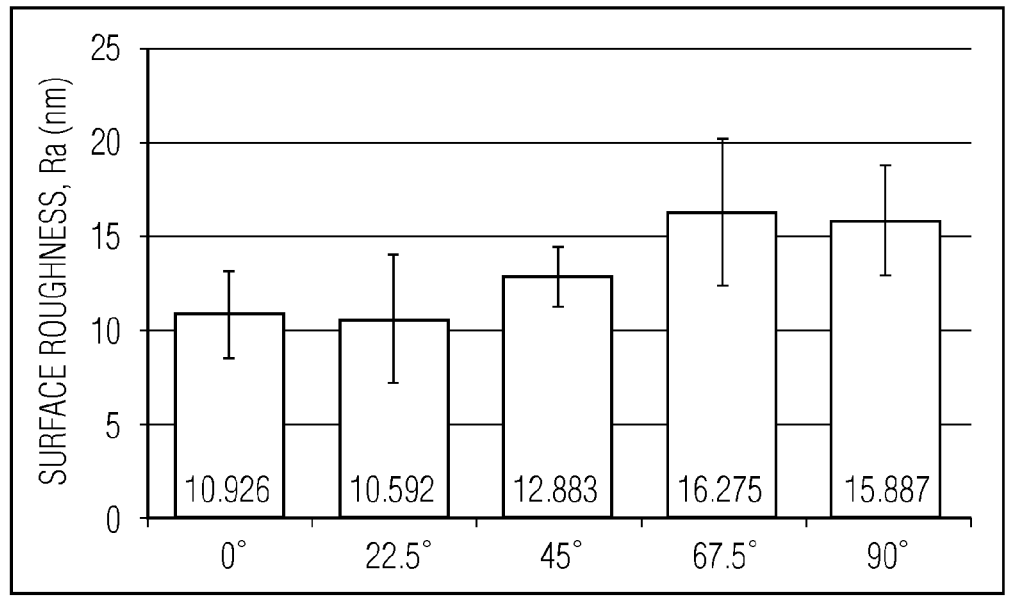
FIG. 8 shows the surface roughness of the polished PVD coating of the present invention on a titanium acetabular cup having a part spherical inner surface with the surface roughness taken at various latitudes about the spherical surface.
Figure 9:
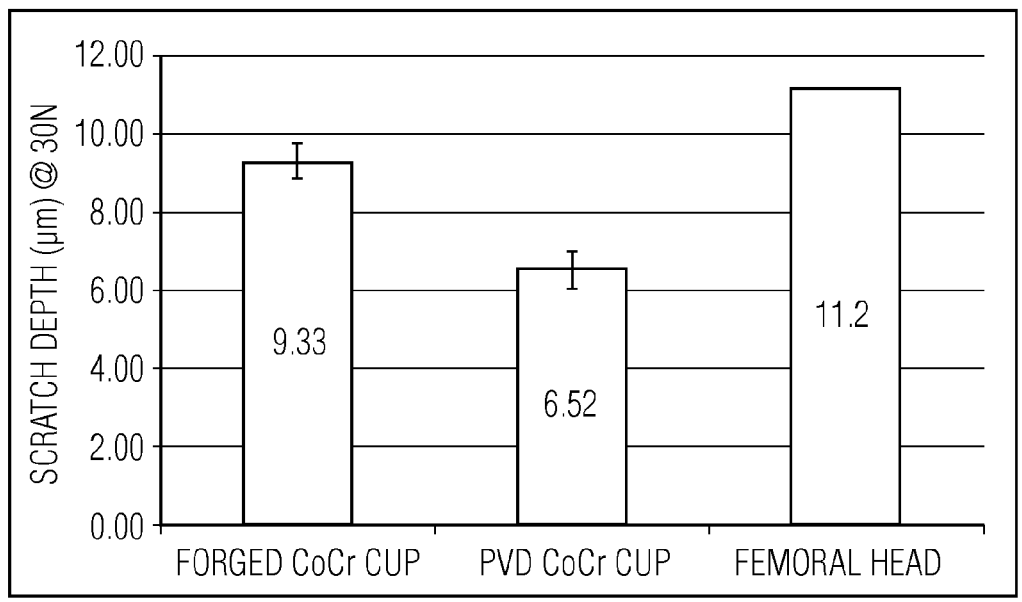
FIG. 9 shows the scratch depth of the PVD coating of the present invention on a titanium acetabular cup as compared to a forged cobalt-chrome cup and a zirconium oxide femoral head.

Referring to FIG. 6, there is shown the tensile bond strength of the coating of the present invention on commercially pure titanium versus soaking time in 40° C. in simulated body fluid. FIG. 7 shows that PVD CoCr coating has the same corrosion behavior as wrough CoCr (ASTM1537). FIG. 8 shows the coating of the present invention on a titanium acetabular cup with a bearing surface polished to a roughness of Ra less than 20 nm. At all latitudes of the spherical inner surface of the cup from the equator (0°) to the pole (90°) the surface roughness was less than 20 nm. Referring to FIG. 9 there is shown the scratch depth of the PVD cobalt-chrome coated titanium acetabular cup when compared to a forged cobalt-chrome acetabular cup when used against a zirconium femoral head under a clinically equivalent 30 N load. It can be seen that the PVD coated cup of the present invention has the shallowest scratch depth when compared to the cobalt-chrome cup and the zirconium femoral head.

Table 1 below provides a summary of the performance of the PVD cobalt-chrome molybdenum coating of the present invention compared to a forged cobalt-chrome cup.

TABLE 1

PVD CoCr coating and device performance vs. Forged CoCr

| Performance | PVD CoCr Coating | Forged CoCr Cup |
|---|---|---|
| Chemical composition | ASTM F 1537 | ASTM F 1537 |
| Phase composition | Major HCP, minor FCC 0.1-1.0 μm grain size | Major FCC, minor HCP 5-50 μm grain size |
| Coating thickness | 13 μm, polishing surface | N/A |
| Coating density | Fully dense | Fully dense |
| Corrosion (ASTM 2129) | Same as wrought CoCr F1537 | Wrought CoCr F 537 |
| Residual Stress | 47 ksi | N/A |
| Hardness (25 g load) | 814 ± 64 DPH | 470 ± 14 DPH |
| Scratch Depth (30N) | 6.5 μm | 9.3 μm |
| Critical load of scratch | 55N for 9.5 μm coating | N/A |
| Mercedes test | HF-1 (highest grade) | N/A |
| Bending crack test | No coating separation | N/A |
| Bond strength | >110 MPa | N/A |
| Surface roughness | <20 nm | <20 nm |
| Device Performance | PVD CoCr Coated Ti | |
| Jim contact fatigue | 10 Mc, passed | |
| Impingement fatigue | 10 Mc, passed | |

The process for applying the cobalt-chrome coating of the present invention may be those described in U.S. Pat. Nos. 4,798,765, 5,077,140, 5,098,540, and 5,955,151 the disclosures of which are incorporated herein by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for manufacturing a prosthetic implant comprising:
   providing a substrate comprising titanium;
   coating a surface of the substrate with a cobalt-chromium molybdenum alloy by multi-arc physical vapor deposition to produce a majority of grains having a hexagonal close pack (HCP) phase, the cobalt-chrome molybdenum alloy comprising about 66 weight percent cobalt, 27.9 weight percent chromium, and about 5.1 weight percent molybdenum; and
   polishing the cobalt-chromium molybdenum HCP coating.

2. The method as set forth in claim 1 wherein the grain sizes are between 0.1 and 1.0 μm.

3. The method as set forth in claim 1 wherein the substrate is a commercially pure titanium or a titanium alloy.

4. The method as set forth in claim 1 wherein the HCP grains have a columnar grain structure wherein the grains have a length which is perpendicular to the substrate surface.

5. The method as set forth in claim 4 wherein the columnar grains are about 1 μm long and 0.1 nm wide.

6. The method as set forth in claim 1 wherein the polishing is performed by a polishing process selected from the group consisting of a media polishing process, a sequential grade SiC wheel grinding an $Al_2O_3$ slump polishing process and a soft wheel polishing process.

7. The method as set forth in claim 6 wherein the surface roughness is Ra<50 nm after polishing.

8. The method as set forth in claim 6 wherein the surface roughness is Ra<25 nm.

9. The method as set forth in claim 1 wherein the polished cobalt-chrome HCP coating has a hardness greater than 500 Vickers Diamond Pyramid Hardness (DPH) at a 25 g load.

10. The method as set forth in claim 1 wherein the coating is greater than 30% chromium plus molybdenum.

11. The method as set forth in claim 1 wherein the cobalt-chrome molybdenum alloy coating is between 6 and 100 μ00 m before polishing.

12. The method Os set forth in claim 11 wherein the cobalt-chrome molybdenum alloy coating is between 5 and 95 μm thick after polishing.

* * * * *